United States Patent
Hershey et al.

(10) Patent No.: US 10,085,922 B2
(45) Date of Patent: *Oct. 2, 2018

(54) ENTERAL FEEDING CATHETER ASSEMBLY INCORPORATING AN INDICATOR

(71) Applicant: Avent, Inc., Alpharetta, GA (US)

(72) Inventors: Adrienne A. Hershey, Cumming, GA (US); Donald J. McMichael, Roswell, GA (US); John A. Rotella, La Jolla, CA (US)

(73) Assignee: Avent, Inc., Alpharetta, GA (US)

( * ) Notice: Subject to any disclaimer, the term of this patent is extended or adjusted under 35 U.S.C. 154(b) by 347 days.

This patent is subject to a terminal disclaimer.

(21) Appl. No.: 14/853,145

(22) Filed: Sep. 14, 2015

(65) Prior Publication Data

US 2016/0000658 A1    Jan. 7, 2016

Related U.S. Application Data

(62) Division of application No. 12/645,553, filed on Dec. 23, 2009, now Pat. No. 9,132,064.

(51) Int. Cl.
*A61J 15/00* (2006.01)
*A61M 25/10* (2013.01)
(Continued)

(52) U.S. Cl.
CPC ......... *A61J 15/0049* (2013.01); *A61J 15/003* (2013.01); *A61J 15/0015* (2013.01);
(Continued)

(58) Field of Classification Search
CPC ...... A61M 25/10187; A61M 25/10188; A61M 2039/085; A61M 16/0434; A61M 16/044;
(Continued)

(56) References Cited

U.S. PATENT DOCUMENTS

| | | |
|---|---|---|
| 3,409,016 A | 11/1968 | Foley |
| 3,630,198 A | 12/1971 | Henkin |

(Continued)

FOREIGN PATENT DOCUMENTS

| | | |
|---|---|---|
| DE | 42 37 978 | 2/1994 |
| EP | 2 060 793 | 5/2009 |

(Continued)

*Primary Examiner* — Nathan R Price
*Assistant Examiner* — Anh Bui
(74) *Attorney, Agent, or Firm* — Dority & Manning, P.A.

(57) ABSTRACT

A catheter assembly incorporating a pre-biased indicator, the assembly includes a catheter having a proximal end, a distal end, and catheter walls defining a catheter lumen. The assembly further includes a base located at the proximal end of the catheter, the base defining an opening to the catheter lumen, the base having a first end and a second end. An inflatable balloon having a predetermined fill volume is located at a distal end of the catheter. An inflation valve is located on the base; the inflation valve is in fluid communication with the balloon through an inflation lumen defined by the catheter walls. The pre-biased indicator located on the base in fluid communication with the balloon is configured to provide a discrete visual signal that the pressure of a fluid in the balloon is different from a predetermined level of pressure or the volume of the balloon is different from the predetermined fill volume.

12 Claims, 9 Drawing Sheets

(51) Int. Cl.
*A61M 16/04* (2006.01)
*G01L 7/06* (2006.01)
*A61M 39/08* (2006.01)

(52) U.S. Cl.
CPC ....... *A61J 15/0042* (2013.01); *A61J 15/0065* (2013.01); *A61J 15/0088* (2015.05); *A61J 15/0092* (2013.01); *A61M 16/044* (2013.01); *A61M 16/0434* (2013.01); *A61M 25/1018* (2013.01); *A61M 25/10184* (2013.11); *A61M 25/10185* (2013.11); *A61M 25/10187* (2013.11); *A61M 25/10188* (2013.11); *G01L 7/063* (2013.01); *A61J 2200/76* (2013.01); *A61M 2039/085* (2013.01); *A61M 2210/1053* (2013.01)

(58) Field of Classification Search
CPC .. A61J 15/0049; A61J 15/003; A61J 15/0034; A61J 15/0038; A61J 15/0042; A61J 2015/0088
USPC ......... 604/100.01, 100.02, 910, 97.03, 99.02
See application file for complete search history.

(56) References Cited

U.S. PATENT DOCUMENTS

| | | | |
|---|---|---|---|
| 3,642,005 A | 2/1972 | McGinnis | |
| 3,731,691 A * | 5/1973 | Chen | A61M 16/044 128/207.15 |
| 3,780,693 A | 12/1973 | Parr | |
| 3,980,082 A | 9/1976 | Miller | |
| 4,134,407 A | 1/1979 | Elam | |
| 4,159,722 A * | 7/1979 | Walker | A61M 16/044 128/207.15 |
| 4,178,939 A | 12/1979 | Stephens | |
| 4,245,639 A | 1/1981 | La Rosa | |
| 4,266,550 A | 5/1981 | Bruner | |
| 4,272,368 A | 6/1981 | Foord et al. | |
| 4,277,227 A | 7/1981 | Jenkins | |
| 4,361,107 A | 11/1982 | Gereg | |
| 4,384,584 A | 5/1983 | Chen | |
| 4,502,490 A | 3/1985 | Evans et al. | |
| 4,522,194 A | 6/1985 | Normann | |
| 4,598,707 A | 7/1986 | Agdanowski et al. | |
| 4,793,351 A | 12/1988 | Landman et al. | |
| 4,994,035 A | 2/1991 | Mokros | |
| 5,103,817 A | 4/1992 | Reisdorf et al. | |
| 5,201,755 A | 4/1993 | Klement | |
| 5,218,970 A | 6/1993 | Turnbull et al. | |
| 5,496,311 A | 3/1996 | Abele et al. | |
| 5,792,070 A | 8/1998 | Kauphusman et al. | |
| 6,004,305 A | 12/1999 | Hursman et al. | |
| 6,082,361 A | 7/2000 | Morejon | |
| 6,536,260 B2 | 3/2003 | Williams | |
| 6,732,734 B2 | 5/2004 | Ogushi et al. | |
| 6,878,130 B2 | 4/2005 | Fournie et al. | |
| 6,916,307 B2 | 7/2005 | Willis et al. | |
| 7,018,359 B2 | 3/2006 | Igarashi et al. | |
| 7,182,750 B2 | 2/2007 | Lampropoulos et al. | |
| 7,195,612 B2 | 3/2007 | Van Sloten et al. | |
| 7,331,979 B2 | 2/2008 | Khosravi et al. | |
| 7,383,736 B2 | 6/2008 | Esnouf | |
| 7,404,329 B2 | 7/2008 | Quinn et al. | |
| 7,470,251 B2 | 12/2008 | Shah | |
| 7,713,191 B2 | 5/2010 | Sekiguchi et al. | |
| 2002/0005202 A1 | 1/2002 | Parry | |
| 2002/0045854 A1 | 4/2002 | Royo et al. | |
| 2002/0115962 A1 | 8/2002 | Fawcett | |
| 2003/0225376 A1 | 12/2003 | Fournie et al. | |
| 2004/0097813 A1 | 5/2004 | Williams | |
| 2004/0106899 A1 | 6/2004 | McMichael et al. | |
| 2004/0106901 A1 | 6/2004 | Letson et al. | |
| 2004/0267195 A1 | 12/2004 | Currlin | |
| 2005/0197667 A1 | 9/2005 | Chan et al. | |
| 2006/0271088 A1 | 11/2006 | Alfrhan | |
| 2007/0010787 A1 | 1/2007 | Hackett et al. | |
| 2007/0208301 A1 | 9/2007 | Evard et al. | |
| 2008/0146993 A1 | 6/2008 | Krishna | |
| 2008/0208240 A1 | 8/2008 | Paz | |
| 2008/0228138 A1 | 9/2008 | Van Sloten et al. | |
| 2009/0312701 A1 | 12/2009 | Gobel et al. | |
| 2010/0081991 A1 | 4/2010 | Swisher | |
| 2010/0185155 A1 | 7/2010 | McMichael et al. | |
| 2010/0185159 A1 | 7/2010 | Bagwell et al. | |
| 2010/0204649 A1 | 8/2010 | Miller et al. | |
| 2010/0217185 A1 | 8/2010 | Terliuc et al. | |
| 2010/0228192 A1 | 9/2010 | O'Dea et al. | |
| 2010/0312181 A1 | 12/2010 | O'Dea | |
| 2011/0082444 A1 | 4/2011 | Mayback et al. | |

FOREIGN PATENT DOCUMENTS

| | | |
|---|---|---|
| GB | 2176595 | 12/1986 |
| JP | 2010-148545 | 7/2010 |
| WO | WO 80/01934 | 9/1980 |
| WO | WO 97/32127 | 9/1997 |
| WO | WO 03/101372 | 12/2003 |
| WO | WO 2006/115904 | 11/2006 |
| WO | WO 2007/103681 | 9/2007 |
| WO | WO 2009/135141 | 11/2009 |
| WO | WO 2010/070291 | 6/2010 |

* cited by examiner

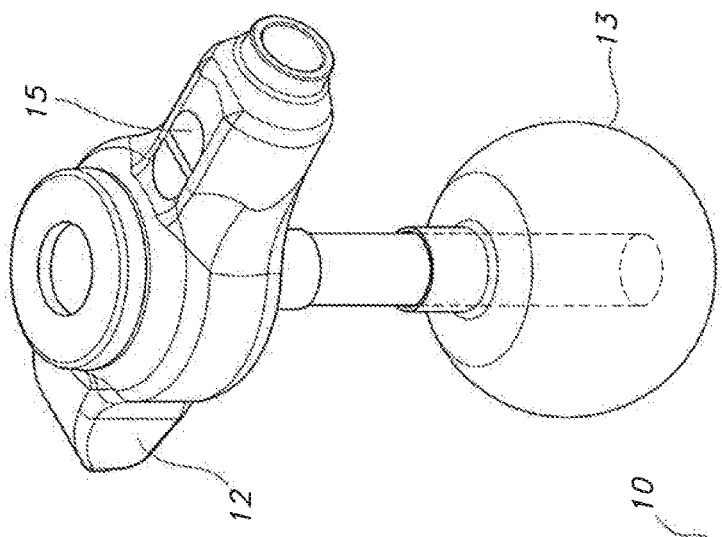
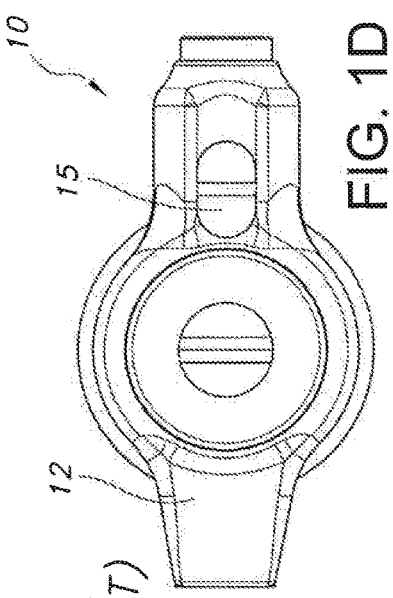
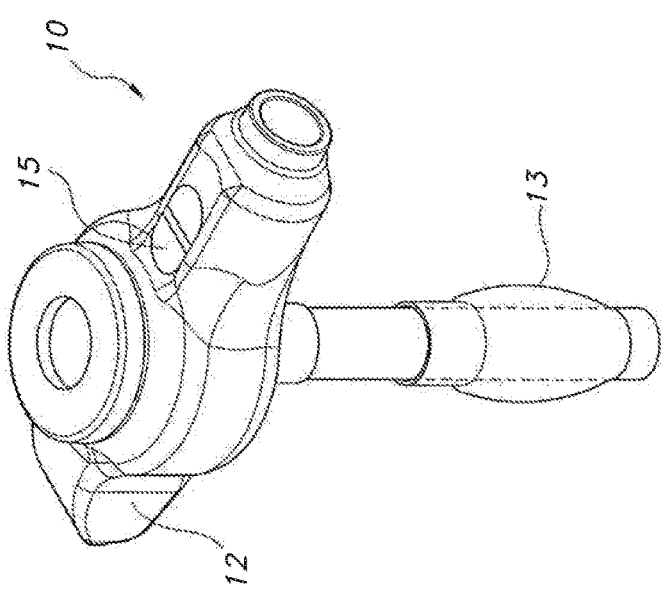
FIG. 1A (PRIOR ART)
FIG. 1B (PRIOR ART)
FIG. 1D (PRIOR ART)

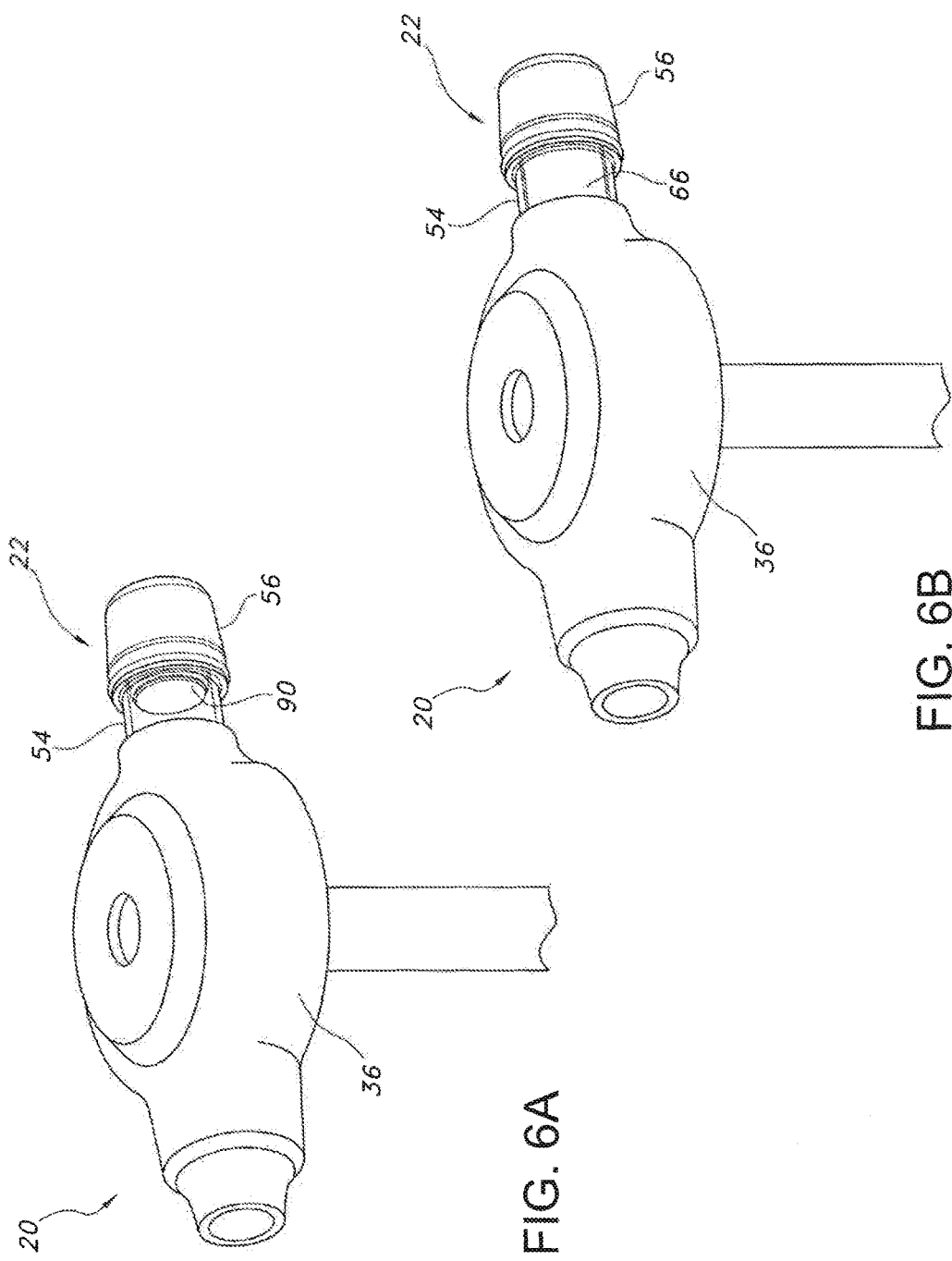

ENTERAL FEEDING CATHETER ASSEMBLY INCORPORATING AN INDICATOR

RELATED APPLICATION

The present application is a Divisional Application of U.S. application Ser. No. 12/645,553, filed Dec. 23, 2009.

FIELD OF THE INVENTION

The present invention relates to improved gastrostomy tubes or enteral feeding catheters.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is common referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transport catheters or tubes are frequently referred to as "gastrostomy tubes", "percutaneous gastrostomy catheters", "PEG tubes" or "enteral feeding catheters".

To prevent the PEG tube from being pulled out of the stomach/intestinal wall, various types of retainers are used at a distal end of the catheter. Examples of conventional devices with Malecot tips or similar expanding tips are found at, for example, U.S. Pat. No. 3,915,171 for "Gastrostomy Tube" issued to Shermeta; U.S. Pat. No. 4,315,513 for "Gastrostomy and Other Percutaneous Transport Tubes" issued to Nawash et al.; U.S. Pat. No. 4,944,732 for "Gastrostomy Port" issued to Russo; and U.S. Pat. No. 5,484,420 for "Retention Bolsters for Percutaneous Catheters" issued to Russo. Exemplary commercial products include the Passport® Low Profile Gastrostomy Device available from Cook Medical, Inc. of Bloomington, Ind. and the Mini One™ Non-Balloon Button available from Applied Medical Technology, Inc. of Brecksville, Ohio. A shortcoming of these devices relates to the manner of insertion and withdrawal of a catheter or tube incorporating these retaining fixtures (e.g., a gastrostomy tube) into a body lumen such as into the stomach.

Balloons can be used in place of these conventional devices with Malecot tips or similar expanding tips. A balloon, typically made of a "soft" or elastomeric medical grade silicone, is attached to the end of the catheter and is deflated for insertion through the stoma and then inflated to hold the enteral feeding assembly in position. While these balloons have many advantages, balloons may eventually leak and deflate. In addition, "soft" or elastomeric medical grade silicone has a tendency to "creep" or stress relax over time which can change the dimensions of the balloon.

Various types of medical devices incorporating inflatable balloons devices are known and widely used in the medical field. For example, endotracheal tubes and tracheostomy tubes utilize inflatable balloons to create a seal that prevents the passage of mucus into the lungs. Pilot balloons, pressure gauges, and inflation indicators are used to provide a continuous reading of the pressure in the balloon in these devices. That is, these devices provide an output that conveys continuous or uninterrupted information showing pressure increases and decreases in the balloon. These devices are described at, for example, U.S. Pat. No. 3,642,005 for "Endotracheal Tube With Inflatable Cuff" issued to McGinnis.; U.S. Pat. No. 4,266,550 for "Pressure Indicators For Inflatable Cuff-Type Catheters" issued to Bruner.; U.S. Pat. No. 6,732,734 for "Pilot Balloon For Balloon Catheters" issued to Ogushi et al.; and U.S. Pat. No. 7,404,329 for "Pressure Gauge For Use With An Airway Lumen" issued to Quinn et al.

In addition to pilot balloons, pressure indicators incorporating bellows or diaphragms are known and electronic pressure indicators are known. For example, a simple bellows pressure indicator for showing continuous reading of fluid pressure is described in U.S. Pat. No. 3,780,693 for "Visible Fluid Pressure Indicator" to Parr. U.S. Pat. No. 7,383,736 "Device and Method for Pressure Indication" issued to Esnouf, describes a bellows device for use with a laryngeal mask balloon or other airway management equipment incorporating balloons. The device of Esnouf incorporates a bellows that is displaced by a differential pressure between the outside of the bellows and the inside of the bellows to provide a continuous reading of the increases and decreases in the pressure of fluid in the balloon. U.S. Pat. No. 7,018,359 for "Inner Pressure Indicator of Cuff" issued to Igarashi et al., describes a bellows or spring structure for use with a tracheostomy tube balloon or endotracheal tube. The device of Igarashi et al. is connected to the balloon through an inflation tube and has an inflation valve at the other end that is connected to a syringe. The device uses a bellows and/or spring indicator provide a continuous reading and display of the increase and decrease in the pressure of fluid in the balloon through movement of the bellows against a numerical scale printed on the housing. U.S. Pat. No. 5,218,970 for "Tracheal Tube Cuff Pressure Monitor" issued to Turnbull et al. describes a continuous pressure monitor for a tracheal tube incorporating an electronic pressure sensor such as a silicon strain gauge pressure sensor, a processor that performs various calibration, scaling and calculation operations on the signal from the sensor and provides an output to a numeric display conveying a continuous reading of the increases and decreases in the pressure of fluid in the balloon.

These indicators are adapted for airway devices where careful and constant monitoring of balloon pressure is important. In order to adequately seal the space between the lumen of the trachea and the balloon, there is a tendency to overinflate the balloon which may result in tissue damage. If the pressure is too low, the balloon does not adequately seal the space between the lumen of the trachea and the balloon thereby allowing secretions to enter the lungs causing pneumonia and other respiratory complications. In order to provide careful control of the balloon pressure, these pilot balloons, bellows and diaphragms indicators and electronic sensors are designed to convey a continuous reading of the increases and decreases in the pressure of fluid in the balloon.

While this level of sensitivity and continuous reading is desirable, pilot balloons and similar bellows or diaphragm indicators are relatively large and typically require skill and experience to accurately interpret the output of these conventional devices as they provide a continuous reading of pressure. While electronic pressure sensors are accurate and are generally easy to read, they are relatively large and expensive. Scaling these types of devices down to a sufficiently small size so they can be used with a low-profile PEG tube only highlights the problems associated with the size, calibration, accuracy, and reading or interpreting the output of these devices.

U.S. Pat. No. 6,878,130 for "External Inflation Indicator for a Low Profile Gastrostomy Tube" issued to Fournie et al. describes an external inflationary indicator similar to a pilot balloon integrated into the base of a gastrostomy device having a retainer balloon. The device of Fournie et al. provides a continuous tactile reading of the inflationary state of the retainer balloon. The Fournie et al. device utilizes two generally bubble-like portions that assume a generally convex shape when the retainer balloon is inflated and a generally concave shape when the balloon is deflated. The changing shape of these generally bubble-like portions provides a continuous tactile indication or reading of the inflationary state of the balloon. In addition, the external inflationary indicator provides continuous visual indication of the inflationary state of the retainer balloon through the use of a separating bar dividing these two generally bubble-like portions of the indicator. The separating bar visually separates as the balloon becomes fully inflated to indicate the inflationary state. Such continuous indication of the inflationary state is important for conventional PEG tube retainer balloons made of elastic materials such as "soft" or elastomeric medical grade silicone because these elastic materials must stretched to increase the balloon volume. Relatively large changes in pressure are needed to stretch such elastic materials from an un-stretched state to expand the balloon. Moreover, the relationship between the amount of pressure needed to stretch such elastic materials to expand the balloon and the volume of the balloon is nonlinear. That is, and the correlation between the pressure of the fluid inside the balloon and the volume of the balloon is not simple which leads to the use of continuous indicators designs such as those described by Fournie et al., if any indicator is used at all.

For example, FIG. 1A is an illustration of a conventional PEG tube device 10 having a base 12 and retainer balloon 13 made of conventional "soft" or elastomeric medical grade silicone in an un-stretched state (i.e., un-inflated condition). A pilot-balloon type indicator 15 as generally described by Fournie et al. is located in the base 12 of the conventional PEG tube device 10. FIG. 1B is an illustration of a conventional PEG tube device 10 having a base 12 and retainer balloon 13 made of conventional "soft" or elastomeric medical grade silicone which has been stretched by inflation to an inflated volume. A pilot-balloon type indicator 15 as generally described by Fournie et al. is located in the base 12 of the conventional PEG tube device 10. FIG. 1C is an illustration showing an exemplary relationship between the pressure of a fluid inside such an elastic retainer balloon and the balloon volume during the stretching the conventional "soft" or elastomeric medical grade silicone forming the balloon by increasing the pressure of a fluid inside the balloon. The illustration is a pressure versus volume plot for a Kimberly-Clark® Mic-Key® 12 french low profile gastrostomy feeding tube with a silicone balloon. As can be seen in FIG. 1C, stretching such elastic balloons from negligible volume (i.e., a deflated condition) at negligible pressure to a deployed volume between about 3 to about 5 milliliters requires an initially large and continuous change in pressure to overcome the resistance to stretching. In this example, an immediate pressure change from zero or negligible pressure to between about 4 to 7 pounds per square inch (28 to 48 kilopascals) is needed to overcome the resistance to stretching needed to inflate such exemplary conventional retainer balloons to a volume of even 1 cubic centimeter (approximately 1 milliliter) and a pressure between about 5 to 10 pounds per square inch (34 to 69 kilopascals) to inflate such conventional "soft" or elastomeric medical grade silicone balloons to a volume of about 3 cubic centimeters (~3 milliliters) with sterile water—although saline solution or air can be used.

Integrating a pilot-balloon type indicator such as described by Fournie et al. or a bellows system or similar graduated indicator as previously described into the base of a low-profile PEG tube device which provides a continuous reading of the pressures encountered by such elastic balloons during stretching requires separating bars, indicator lines or similar components on the flexible membrane that provide information based on very small movements—typically less than one millimeter. Using such a small scale to provide a continuous reading of the inflationary state of the retainer balloon makes it difficult to read and view properly, especially at inflating pressure less than 4 pounds per square inch (less than 28 kilopascals). For example, the base of a typical low-profile PEG tube is approximately 1.625 inches (~41 mm) in length, approximately 0.75 inches (~19 mm) in width and approximately 0.5 inches (~13 mm) in depth. Referring to FIG. 1D which corresponds to FIG. 3 of Fournie, et al., comparing the relative dimensions of the pilot-balloon type indicator 15 located in the base 12 of the conventional PEG tube device 10 with the base dimensions noted above provides a context in which to understand that the small size of the pilot-balloon type indicator 15 would be impractical. For example, the pilot-balloon type indicator would appear to have dimensions of approximately 6 mm in length, approximately 5 mm in width and the separating bar on the indicator would appear to have a width of approximately 0.8 mm (about the diameter of the medium size ball-tip from the tip of a ball point pen or the diameter of a pencil lead from a mechanical pencil).

Accordingly, there is a need for a pressure change indicator assembly that can be readily integrated into the head of a PEG tube and which is easy to view and read properly and function at pressures less than about 4 pounds per square inch (28 kilopascals). A need exists for a pressure change indicator assembly that be readily integrated into a PEG tube that is simple, reliable and accurate at indicating predetermined volumes as well as easy to understand. A need also exists for a pressure change indicator assembly that be readily integrated into a PEG tube that is simple, reliable and accurate at indicating predetermined pressures as well as easy to understand. There is also an unmet need for a pressure change indicator assembly that conveys a simple and easy to see and understand signal about a change in a deployed balloon, particularly in a balloon deployed at pressures less than about 4 pounds per square inch (28 kilopascals).

SUMMARY OF THE INVENTION

In response to the difficulties and problems discussed herein, the present invention provides a balloon catheter device incorporating an indicator that provides a discrete visual signal about the inflation condition of balloon that is associated with the catheter. For example, the indicator provides a discrete visual signal that the volume of the balloon is different from a predetermined volume. Alternatively and/or additionally, the indicator may provide a discrete visual signal that the pressure of a fluid in the balloon is different from a predetermined level of pressure. This present invention provides particular advantage for a balloon catheter device that incorporates a balloon having a predetermined fill volume at relatively low pressures (e.g., 4 pounds per square inch (28 kilopascals) or less).

According to an aspect of the invention, the balloon catheter device may be an enteral feeding catheter assembly that includes a catheter having a proximal end, a distal end, and catheter walls defining a catheter lumen. A base is located at the proximal end of the catheter. The base defines an opening to the catheter lumen. The base itself has a first end and a second end. The assembly includes an inflatable balloon located at a distal end of the catheter. A characteristic feature of the inflatable balloon is that is has a predetermined fill volume. Such inflatable balloons are readily distinguishable from conventional elastic balloons (e.g., soft elastic silicone) typically used with enteral feeding catheters. Generally speaking, the predetermined fill volume is the same as or no more than about 1.5 times (i.e., about 50 percent greater than) the volume achieved by expanding a balloon having an initially collapsed, folded, non-distended state to a state in which the material that forms the balloon is smooth and completely unfolded but prior to any meaningful stretching or distending of that material. That is, the predetermined fill volume is the same as or no more than about 1.5 times (i.e., about 50 percent greater than) the volume of the balloon at the transition from its non-distended state to its distended state.

The assembly includes an inflation valve located on the base. The inflation valve is in fluid communication with the balloon. This may be accomplished through an inflation lumen, defined by a portion of the wall of the catheter, extending from the balloon to the inflation valve. An external inflation lumen or other configurations are contemplated. The inflation valve may desirably be located on the first end of the base.

The assembly also includes a pre-biased indicator located on the base in fluid communication with the balloon. According to the invention, the pre-biased indicator is configured to provide a discrete visual signal that the pressure of a fluid in the balloon has changed from a predetermined level of pressure. Alternatively and/or additionally, the pre-biased indicator is configured to provide a discrete visual signal that the volume of the balloon has changed from a predetermined volume. For example, the pre-biased indicator may be configured to provide a discrete visual signal that the volume of the balloon is less than a predetermined fill volume.

The indicator may be located on the second end of the base. It is contemplated that the indicator may be located on the first end of the base. In an aspect of the invention, the pre-biased indicator may be in fluid communication with the balloon through an indicator lumen, defined by a portion of the wall of the catheter, extending from the balloon to the indicator. Alternatively and/or additionally, the pre-biased indicator may be in fluid communication with the balloon through the inflation lumen, defined by a portion of the wall of the catheter, extending from the balloon to the inflation valve and the indicator.

The pre-biased indicator of the enteral feeding catheter assembly may include a housing having a first end, a second end, one or more walls defining an interior channel, and an axial dimension. The first end of the housing is in fluid communication with the inflatable balloon. Desirably, at least a portion of the housing is transparent or translucent.

The pre-biased indicator further includes a flexible sleeve positioned within the interior channel of the housing. The flexible sleeve has a first surface, an opposed second surface, a first end located within the interior channel of the housing, a second end engaged with the housing to create a fluid impervious seal, and a flexible, generally annular portion joining the first end and second end of the sleeve.

According to the invention, the flexible, generally annular portion of the flexible sleeve defines a rolling annular fold intermediate the first end and the second end of the sleeve. The rolling annular fold is configured so that at least a portion of the first surface of the flexible sleeve is generally adjacent the one or more housing walls and at least a portion of the second surface of the flexible sleeve defines a sleeve cavity. Generally speaking, the rolling annular fold travels as the sleeve moves in the axial direction of the housing. That is, movement of the flexible sleeve in an axial direction causes a portion of the second surface of the flexible sleeve to evert or turn inside out at the rolling annular fold so that it becomes directly adjacent the one or more housing walls.

The assembly also includes a biasing element located at least partially within the sleeve cavity and between the first end of the housing and the second end of the housing. The biasing element is configured to deform at a defined force that corresponds to a predetermined fill volume so the flexible sleeve moves from a first axial position to at least a second axial position to provide a discrete visual signal that the pressure of a fluid in the balloon is different from an inflation pressure that corresponds to the predetermined fill volume. The biasing element is a deformable device or component that distorts due to compressive forces yet recovers to its original shape when the compressive forces are removed. The biasing element may be a spring, such as a coil spring, a plurality of springs, an elastomeric body or the like. The biasing element may have a spring rate or a deformation rate or tripping point of between about 0.1 lbs-force/inch to about 1.0 lbs-force /inch (about 0.1 newtons/cm to about 1.8 newtons/cm) which provides a discrete signal of change in pressure, particularly for pressures below about 4 pounds per square inch (psi) (about 28 kilopascals), for example, for pressures of from 1 to about 3.5 pounds per square inch (approximately 7 to about 25 kilopascals), or as another example, for pressures of from about 2 to about 3 pounds per square inch (approximately 14 to about 21 kilopascals).

The present invention also encompasses a balloon catheter device that is composed of a catheter having a proximal end, a distal end, and catheter walls defining a catheter lumen; a base located at the proximal end of the catheter defining an opening to the catheter lumen; an inflatable balloon having a predetermined fill volume, the balloon located at a distal end of the catheter and configured to contain a fluid under pressure; an inflation valve located on the base, the inflation valve in fluid communication with the balloon; and a pre-biased indicator in fluid communication with the balloon. According to the invention, the pre-biased indicator is configured to provide a discrete visual signal that the pressure of a fluid in the balloon has changed from a predetermined level of pressure. Alternatively and/or additionally, the pre-biased indicator is configured to provide a discrete visual signal that the volume of the balloon has changed from a predetermined volume. For example, the pre-biased indicator may be configured to provide a discrete visual signal that the volume of the balloon is less than a predetermined fill volume The present invention encompasses an indicator assembly for use in medical devices having a balloon that contains a pressurized liquid. The indicator assembly is especially for medical devices having a head located outside the human body and an inflatable retainer balloon for deployment within a lumen of a human body. The indicator assembly includes an inflatable thin-walled balloon having a predetermined fill volume. The balloon is configured to contain a fluid under pressure upon inflation to its predetermined fill volume and after inflation further configured to contain a reserve volume of fluid that is less than the predetermined fill volume when the fluid is no longer under pressure. Desirably, the pressure of the fluid upon inflation is at relatively low pressures (e.g., 4 pounds per square inch (28 kilopascals) or less).

The indicator assembly also includes a pre-biased indicator that provides only a first discrete visual signal when the balloon is inflated to its predetermined fill volume and a second discrete visual signal when the fluid in the balloon is no longer under pressure, with no signal of other inflation states therebetween. That is, the pre-biased indicator provides a signal of only two states of the balloon—that it is at its predetermined fill volume and that the fluid in the balloon is no longer under pressure. According to the invention, the second discrete visual signal provides warning that the balloon volume has reached the reserve volume—which generally corresponds to the volume of the balloon at the transition from its non-distended state to its distended state when the balloon is no longer under pressure or at about the lower limit of the predetermined fill volume. Generally speaking, the predetermined fill volume is desirably from about the reserve volume (i.e., just above the reserve volume) to about 1.5 times greater than the reserve volume (i.e., about the reserve volume to about 50 percent greater than the volume of the balloon at the transition from its non-distended state to its distended state). For example, the predetermined fill volume may be from about 1.01 to about 1.4 times greater than the reserve volume (i.e., about 1 percent to about 40 percent greater than the volume of the balloon at the transition from its non-distended state to its distended state). As another example, the predetermined fill volume may be from about 1.5 to about 1.3 times greater than the reserve volume (i.e., about 5 percent to about 30 percent greater than the volume of the balloon at the transition from its non-distended state to its distended state).

DEFINITIONS

As used herein the following terms have the specified meanings, unless the context demands a different meaning or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the phrase "fluid communication" means a transmission or passage for a between two points and/or two structures for a specific purpose. In this example, fluid communication would be a passage which permits liquids and/or gasses to pass.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the terms "align," "aligned," and/or "alignment" refers to the spatial property possessed by an arrangement or position of things in a straight line.

As used herein, the terms "orientation" or "position" used interchangeably herein refer to the spatial property of a place where something is situated or a way in which something is situated; for example, "the position of the hands on the clock."

As used herein, the term "about" adjacent to a stated number refers to an amount that is plus or minus ten (10) percent of the stated number.

As used herein, the term "non-distended" when used with respect to a catheter balloon refers to a catheter balloon which has no radial pressure applied to the balloon's inner surface that is greater than atmospheric pressure or the pressure of the environment immediately surrounding the exterior of the balloon. Non-distended catheter balloons include, for example, a catheter balloon which does not contain a fluid, or which contains a fluid that is not under pressure or a pressure that is less than or equal to atmospheric pressure or the pressure of the environment immediately surrounding the exterior of the balloon. In contrast, the term "distended" when used with respect to a catheter balloon refers to a catheter balloon which is being subjected to pressure applied to the balloon's inner surface that is greater than atmospheric pressure or the pressure of the environment immediately surrounding the exterior of the balloon, such as pressure exerted by a fluid (e g., pressurized liquid or gas) contained within the catheter balloon.

As used herein, the term "predetermined fill volume" when used with respect to a catheter balloon refers to a volume in a range with a lower limit at the transition from a non-distended state to a distended state where the fluid in the balloon is first under pressure and a upper limit that is no more than about 1.5 times (i.e., about fifty percent (50%) greater than) the volume of the balloon at the transition from a non-distended state to a distended state. For example, a predetermined fill volume can be the volume of the balloon at the transition from a non-distended state to a distended state and may encompass a volume of up to about 1.4 times (i.e., about forty percent (40%) greater than) the volume of the balloon at the transition from a non-distended state to a distended state. As another example, a predetermined fill volume can be the volume of the balloon at the transition from a non-distended state to a distended state to a volume up to about 1.2 times (i.e., about twenty percent (20%) greater than) the volume of the balloon at the transition from a non-distended state to a distended state. Conventional elastic balloons which continually distend with increasing pressure are considered to not have a predetermined fill volume. While it might be possible to characterize some elastic balloons as having a transition from a non-distended state to a distended state, such a transition occurs only during the earliest introduction of pressure to initiate stretching or continuous distension of the material of the balloon.

These terms may be defined with additional language in the remaining portions of the specification.

BRIEF DESCRIPTION OF THE DRAWINGS

FIG. 1A is a perspective view of an exemplary prior art device.

FIG. 1B is a perspective view of an exemplary prior art device.

FIG. 1D is a top view of a conventional prior art device.

FIGS. 6A and 6B are perspective views showing details of an exemplary enteral feeding catheter assembly incorporating an indicator.

DETAILED DESCRIPTION OF THE INVENTION

Figure 1C:
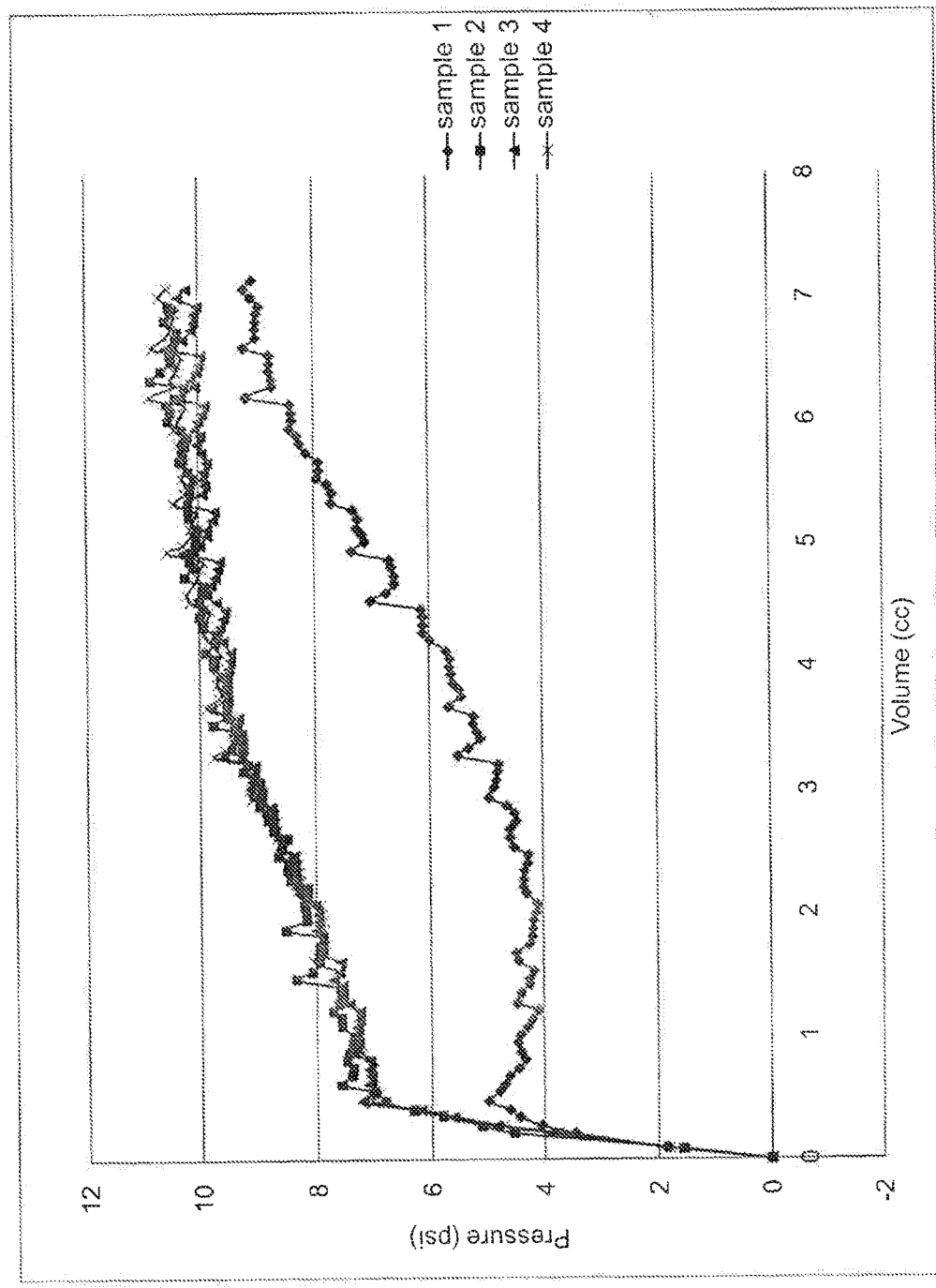
FIG. 1C is an illustration of a feature of a conventional prior art device.

The invention(s) disclosed herein relate generally to improved medical care for patients who require enteral feeding. More particularly, the invention(s) disclosed herein relate to an enteral feeding assembly including an inflatable balloon having a predetermined fill volume for holding at least a portion of the assembly in a body lumen and further incorporating an indicator that provides a discrete visual signal that pressure in the balloon is different from a predetermined level of pressure. The invention(s) disclosed herein may also include an indicator assembly for use with medical devices incorporating inflatable balloons in which the indicator assembly including an inflatable balloon having a predetermined fill volume and further incorporating an indicator that provides a discrete visual signal that pressure in the balloon is different from a predetermined level of pressure.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 2B:
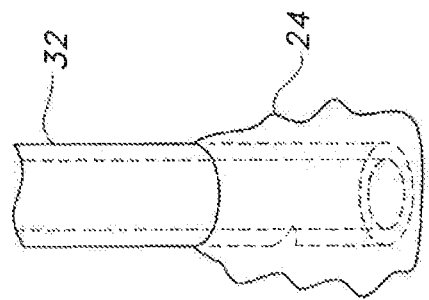
FIG. 2B is a perspective view of a detail of exemplary enteral feeding catheter assembly incorporating an indicator.
Figure 2A:
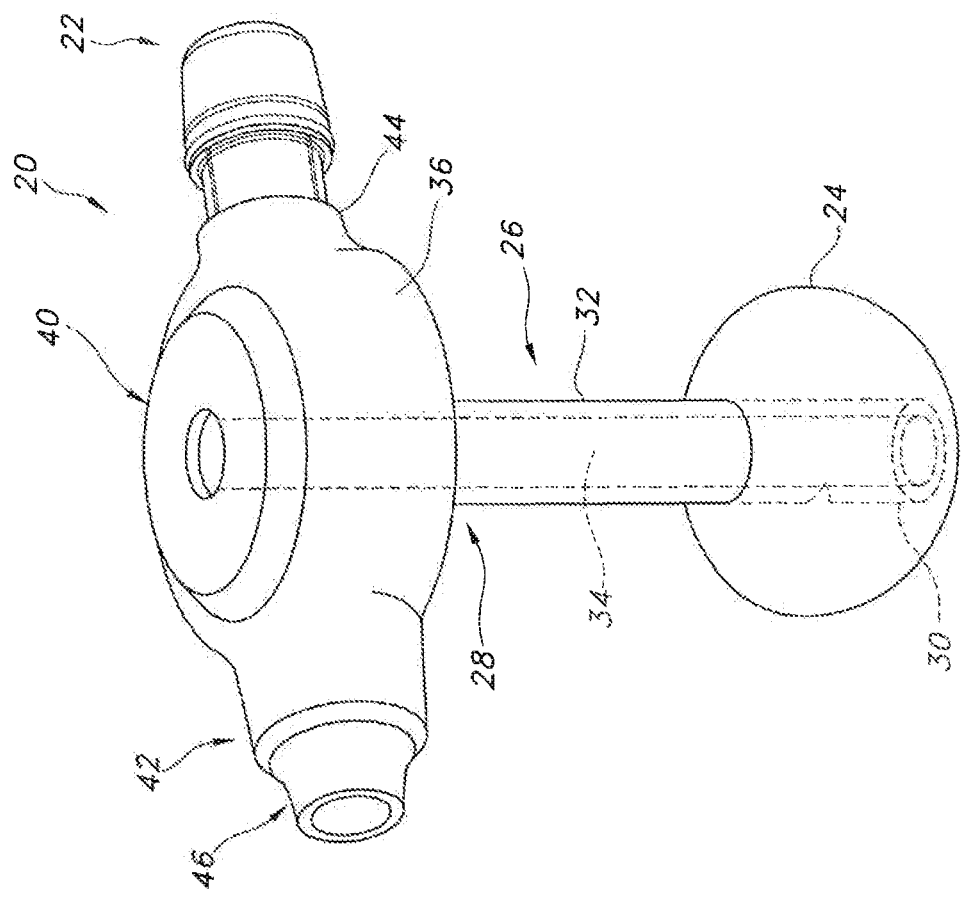
FIG. 2A is a perspective view of an exemplary enteral feeding catheter assembly incorporating an indicator.
Figure 3:
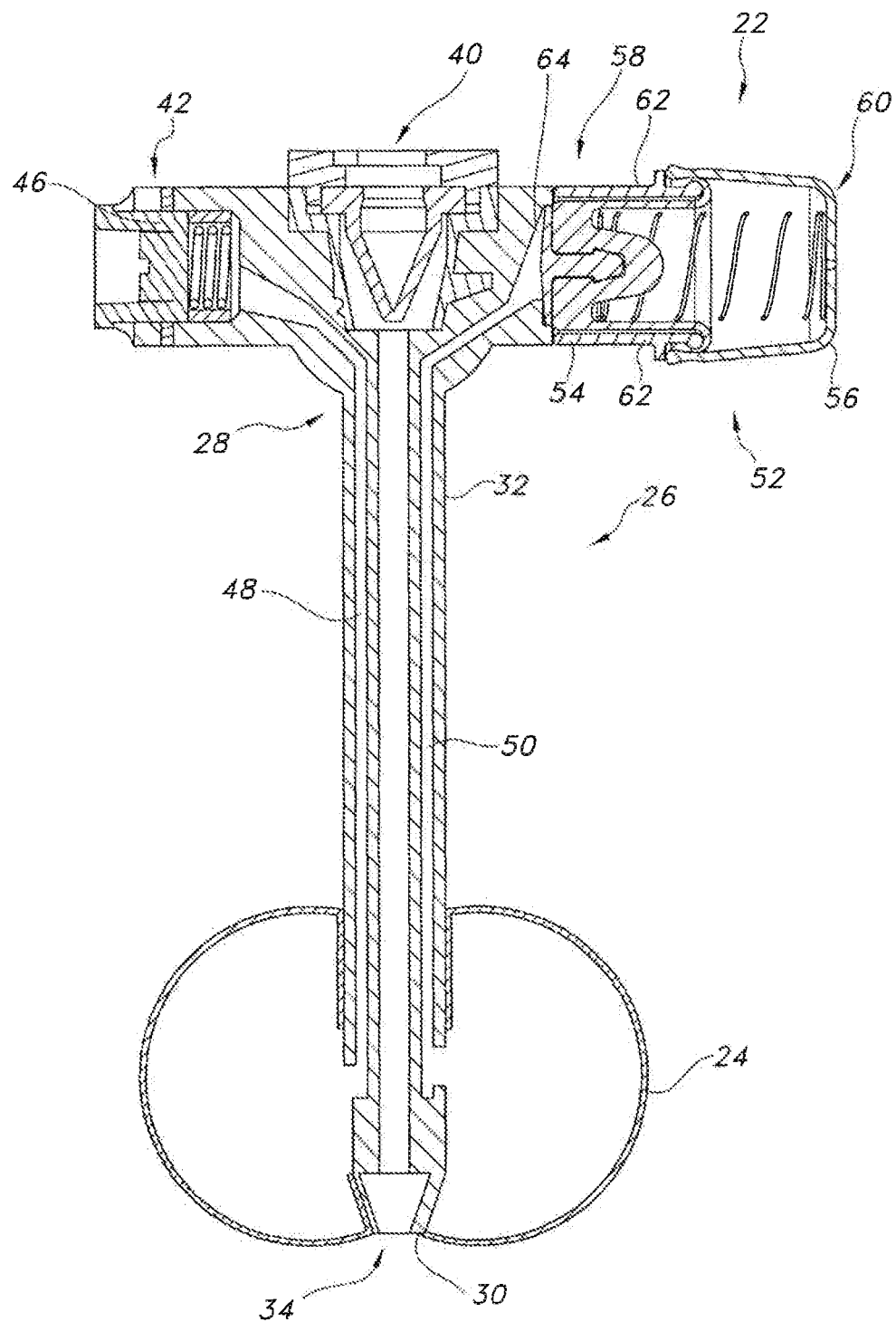
FIG. 3 is a side view showing a cross-section of an exemplary enteral feeding catheter assembly incorporating an indicator.

Turning now to the drawings, the present invention is generally illustrated in FIGS. 2A though 7B. An enteral feeding catheter assembly 20 incorporating a pre-biased indicator 22 that provides a discrete visual signal that pressure in a balloon 24 associated with the catheter 26 is different from a predetermined level of pressure. Alternatively and/or additionally, the pre-biased indicator 22 may be configured to provide a discrete visual signal that the volume of the balloon 24 has changed from a predetermined volume. For example, the pre-biased indicator 22 may be configured to provide a discrete visual signal that the volume of the balloon 24 is less than a predetermined fill volume.

The enteral feeding catheter assembly 20 includes a catheter 26 having a proximal end 28, a distal end 30, and catheter walls 32 defining a catheter lumen 34. A base 36 is located at the proximal end 28 of the catheter 26. The base 36 defines an opening 40 to the catheter lumen 34. The base itself has a first end 42 and a second end 44. The assembly 10 includes an inflatable balloon 24 located at a distal end of the catheter. A characteristic feature of the inflatable balloon 24 is that it has a predetermined fill volume. As noted above, such inflatable balloons having a predetermined fill volume are readily distinguishable from conventional elastic balloons. Generally speaking, during expansion of a balloon having an initially collapsed or crumpled state as generally illustrated in FIG. 2B to the point in which the material that forms the balloon is smooth and unfolded as generally illustrated in FIG. 2A, the predetermined fill volume is a volume in a range having a lower limit at the volume in which the material that forms the balloon is first becomes smooth, unfolded and under a pressure but prior to any stretching or distending of that material and an upper limit that is no more than 50% greater in volume than the lower limit. In other words, the predetermined fill volume is a volume in a range with a lower limit at the balloon's transition from a non-distended state to a distended state and a upper limit that is no more than about 1.5 times (i.e., about fifty percent (50%) greater than) the volume of the balloon at the transition from a non-distended state to a distended state. The volume at the lower limit of this range where the pressure of the fluid in the balloon is essentially zero is the "reserve volume".

The assembly 20 includes an inflation valve 46 located on the base. The inflation valve 46 is in fluid communication with the balloon 24. This may be accomplished through an inflation lumen 48, defined by a portion of the wall 32 of the catheter 26, extending from the balloon 24 to the inflation valve 46. An external inflation lumen or other configurations are contemplated. The inflation valve may desirably be located on the first end 42 of the base.

The pre-biased indicator 22 is located on the base 36 in fluid communication with the balloon 24. According to the invention, the pre-biased indicator 22 is configured to provide a discrete visual signal that the pressure of a fluid in the balloon has changed from a predetermined level of pressure. Alternatively and/or additionally, the pre-biased indicator 22 may be configured to provide a discrete visual signal that the volume of the balloon 24 has changed from a predetermined volume. For example, the pre-biased indicator 22 may be configured to provide a discrete visual signal that the volume of the balloon 24 is less than a predetermined fill volume.

The indicator 22 may be located on the second end 44 of the base 36. It is contemplated that the indicator 22 may be located on the first end 42 of the base fitted in parallel with the inflation valve 46 or in some other arrangement. The pre-biased indicator 22 may be in fluid communication with the balloon 24 through an indicator lumen 50, defined by a portion of the wall 32 of the catheter 26, extending from the balloon 24 to the indicator 22. Alternatively and/or additionally, the pre-biased indicator may be in fluid communication with the balloon through the inflation lumen, defined by a portion of the wall of the catheter, extending from the balloon to the inflation valve and the indicator.

Figure 4:
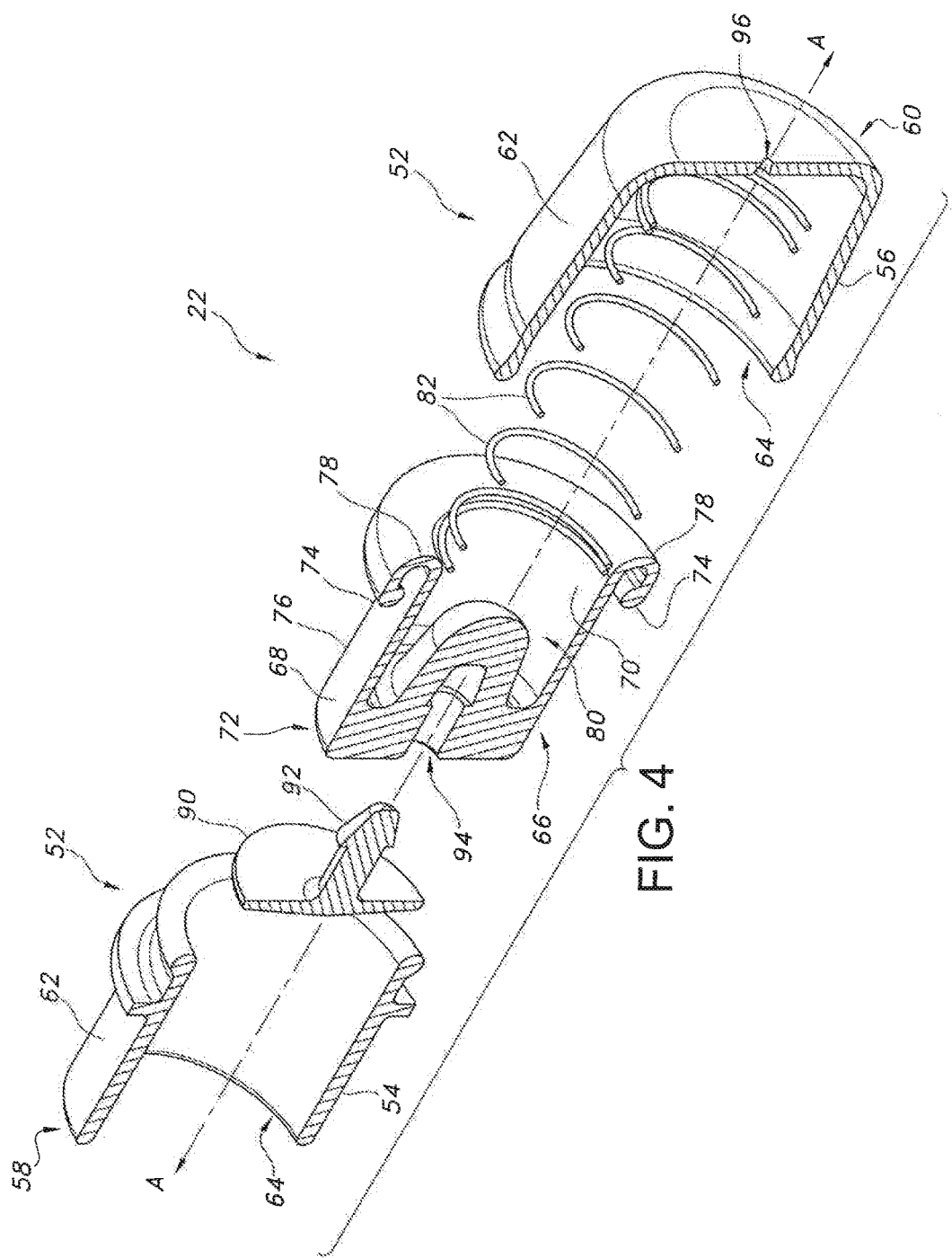
FIG. 4 is a perspective view showing a cross-sectional detail of a feature from an exemplary enteral feeding catheter assembly incorporating an indicator.

Referring to FIG. 4, there is shown in an exploded cross-sectional view, an exemplary pre-biased indicator 22 of the enteral feeding catheter assembly 10. The pre-biased indicator 22 includes a housing 52. The housing 52 may be formed of one-piece. Alternatively, and as shown in FIG. 4, the housing 52 may be composed of multiple sections. For example, the housing 52 may be formed of a lens 54 and a cap 56. Generally speaking, the housing 52 has a first end 58, a second end 60, one or more walls 62 defining an interior channel 64, and an axial dimension "A". The first end 58 of the housing 52 is in fluid communication with the inflatable balloon 24. Desirably, at least a portion of the housing 52 is transparent or translucent. For example, the lens 54 may be transparent or translucent.

The pre-biased indicator 22 further includes a flexible sleeve 66 positioned within the interior channel 64 of the housing 52. The flexible sleeve 66 has a first surface 68, an opposed second surface 70, a first end 72 located within the interior channel of the housing, a second end 74 engaged with the housing 52 to create a fluid impervious seal, and a flexible, generally annular portion 76 joining the first end 72 and second end 74 of the sleeve.

According to the invention, the flexible, generally annular portion 76 of the flexible sleeve defines a rolling annular fold 78 intermediate the first end 72 and the second end 74 of the sleeve. The rolling annular fold 78 is configured so that at least a portion of the first surface 68 of the flexible sleeve is generally adjacent the one or more housing walls 62 and at least a portion of the second surface 70 of the flexible sleeve defines a sleeve cavity 80. Generally speaking, the rolling annular fold 78 travels or moves as the first end 72 of the sleeve 66 travels along the axial direction or dimension "A" of the housing 52. That is, movement of the first end 72 of the flexible sleeve 66 along an axial direction "A" causes a portion of the second surface 70 of the flexible sleeve to evert at the rolling annular fold 78 so that it becomes directly adjacent the one or more housing walls 62.

The pre-biased indicator 22 also includes a biasing element 82 located at least partially within the sleeve cavity 80 and between the first end 58 of the housing and the second end 60 of the housing. The biasing element 82 is configured to deform at a predetermined pressure or force so the flexible sleeve 72 moves from a first axial position to at least a second axial position. The pressure or force is applied against the first end 72 of the flexible sleeve 66. The first end 72 is in fluid communication with the inflatable balloon through an indicator lumen or, in some configurations, an inflation lumen. A detail of this movement of the flexible sleeve is illustrated in cross-sectional view by FIG. 5A and FIG. 5B.

Figure 5B:
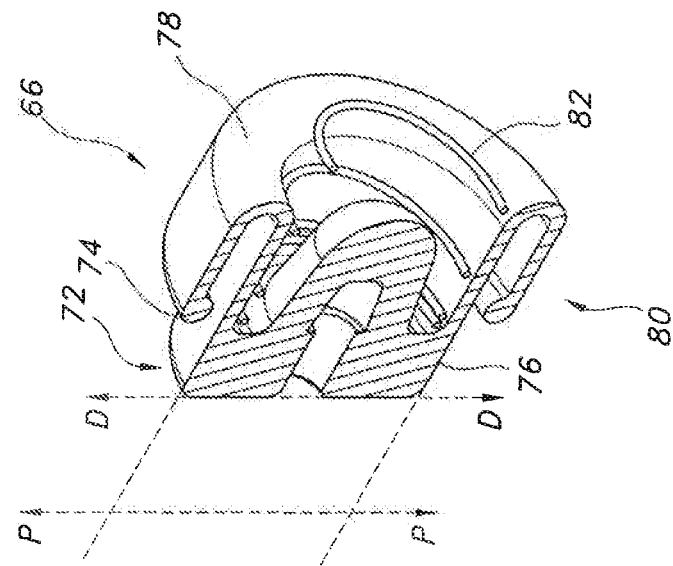
FIGS. 5A and 5B are perspective views showing cross-sectional details of a feature from an exemplary enteral feeding catheter assembly incorporating an indicator.
Figure 5A:
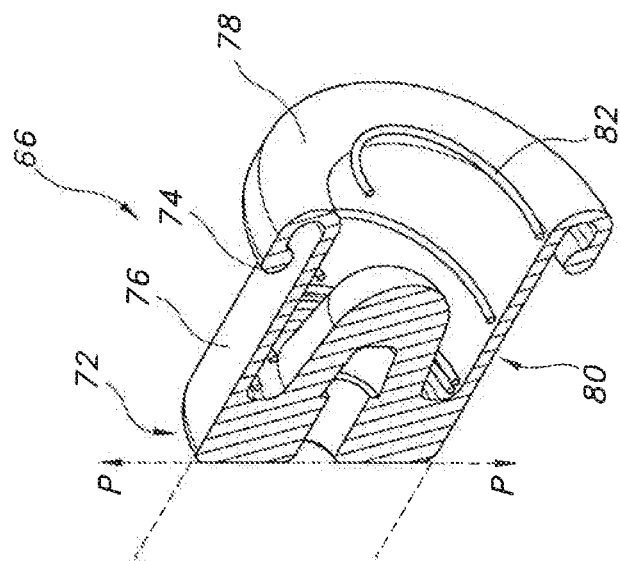

FIG. 5A illustrates a cross section of a flexible sleeve 66 showing the biasing element 82 located at least partially within the sleeve cavity 80 defined by the flexible annular portion 76 prior to deformation of the biasing element. In this configuration, the first end 72 of the flexible sleeve 66 is at a first axial position "P". The second end 74 of the flexible sleeve 66 is near the rolling annular fold 78 and is relatively distant from the first end 72 of the sleeve 66.

FIG. 5B illustrates a cross section of a flexible sleeve 72 showing the biasing element 82 located at least partially within the sleeve cavity 80 defined by the flexible annular portion 76 after deformation of the biasing element. In this configuration, the first end 72 of the flexible sleeve 66 is at a second axial position "D". The second end 74 of the flexible sleeve 66 is relatively further away from the rolling annular fold 78 and is relatively nearer to the first end 72 of the sleeve 66.

During normal use of an enteral feeding assembly, a user utilizes a syringe to add sterile water or some other appropriate liquid, or in some situations, air, through the inflation valve to fill the balloon. The biasing element 82 of the pre-biased indicator deforms due to force (i.e., fluid pressure) against the first end 72 of the flexible sleeve communicated from the balloon through the indicator lumen (or, in some configurations, the inflation lumen). That fluid pressure is generated by filling the balloon past the "reserve volume" at the transition from its non-distended state to its distended state at which point the pressure of fluid in the balloon increases, typically in a linear pressure-volume relationship, until the pressure of the balloon reached the predetermined level of pressure at which the biasing element deforms. The predetermined level of pressure corresponds to the predetermined fill volume, which is a volume in a range with a lower limit at the volume of the balloon at the transition from its non-distended state to its distended state where the fluid in the balloon is first under pressure and an upper limit no more than about 1.5 times (i.e., 50 percent greater than) the volume of the balloon at the transition from its non-distended state to its distended state.

The deformation of the biasing element causes the flexible sleeve to move from its first axial position "P" to its second axial position "D". The result of this movement from a first axial position to a second axial position is illustrated in perspective view by FIGS. 6A and 6B. FIG. 6A illustrates an enteral feeding catheter assembly 20 incorporating a pre-biased indicator 22. In this illustration, the biasing element is deformed due to pressure in the inflatable balloon (not shown in this FIG. 6A) so the flexible sleeve is not visible in the pre-biased indicator 22. More particularly, the flexible sleeve 66 is in the second axial position "D" as generally illustrated in FIG. 5B. The cap 56, the flexible sleeve 66 and the biasing element 82 are sized so that the flexible sleeve 66 is not visible through the cap 56, which desirably is opaque, when the flexible sleeve is in the second axial position "D". This movement of the flexible sleeve to the second axial position "D" where it is not readily visible provides a very simple and reliable indication to a user that the pressure of fluid in the balloon is different from (i.e., above) a predetermined level of pressure. Alternatively and/or additionally, the movement of the flexible sleeve to the second axial position "D" where it is not readily visible provides a very simple and reliable indication to a user that the volume of the balloon is at or greater than a predetermined fill volume. Since the flexible sleeve 66 is impermeable and is engaged with the housing 52 to form a seal, a vent means 96 to maintain atmospheric pressure in the sleeve cavity 80 defined by the flexible annular portion 76 of the flexible sleeve is located at the second end of the housing 60. The vent means 96 may be a hole, a plurality of holes, a slit, a plurality of slits, a highly porous, spongy region or the like. The vent means 96 allows passage of air into and out of the sleeve cavity 80 defined by the second surface 70 of the flexible sleeve at the flexible annular portion 76 located in the interior channel 64 of the housing 52. The passage of air through the vent means 96 is in response to the axial movement of the flexible sleeve.

In an aspect of the invention, the flexible sleeve may include a plate 90 joined to a plug 92 that is adapted to fit into a socket 94 formed in the first end 72 of the flexible sleeve. This plate and the associated plug and socket may be used to provide some dimensional stability to the first end 72 of the flexible sleeve which is in fluid communication with the balloon and which receives pressure that is communicated to the biasing element. The plate 90 may also be configured to have the same color as the material at the second end 60 of the housing 52 (e.g., the cap 56 if a two piece housing is used) so that, when the biasing element is deformed and the flexible sleeve is at its second axial position "D", the material forming the first end 72 of the flexible sleeve is not readily visible because it is hidden beneath the plate 90 and blends in with the second end 60 of the housing 52 so that a user does not misinterpret the position of the sleeve based on the visible presence of the color of the material forming the flexible sleeve.

Referring now to FIG. 6B, there is illustrated an enteral feeding catheter assembly 20 incorporating a pre-biased indicator 22 in a different configuration. In this illustration, the biasing element 82 of the pre-biased indicator 22 is no long deformed due to pressure in the inflatable balloon (not shown in this FIG. 6A). In this configuration, the flexible sleeve is visible through the housing and provides a simple, easy to interpret signal. More particularly, the flexible sleeve 66 is in the first axial position "P" as generally illustrated in FIG. 5A. If the housing 52 is composed of two or more pieces such as, for example, a lens 54 and a cap 56, these components and the flexible sleeve 66 and the biasing element 82 are sized so that the flexible sleeve 66 is visible through the lens 54, which desirably is transparent or translucent, when the fluid pressure in the balloon falls below a predetermined level and the biasing element 82 expands to urge the first end 72 of flexible sleeve 66 back along the interior channel 64 to the first end 58 of the housing 52. In other words, when the fluid pressure in the balloon falls below the predetermined pressure of the biasing element, the biasing element pushes the flexible sleeve back into the first axial position where a user can see the flexible sleeve and readily understand the signal that the pressure in the balloon has fallen below the predetermined level. This movement of the flexible sleeve to the first axial position "P" where it is readily visible provides a very simple and reliable indication to a user that the pressure of fluid in the balloon is different from (i.e., below) a predetermined level of pressure. Alternatively and/or additionally, the movement of the flexible sleeve to the first axial position "P" where it is readily visible provides a very simple and reliable indication to a user that the volume of the balloon is below or less than a predetermined fill volume.

The flexible sleeve is desirably made of a soft, flexible material. Exemplary materials include, but are not limited to, polyurethane, silicone and other materials that are resilient. Desirably, the material has a memory of its shape.

Suitable materials include, but are not limited to, "soft" or elastomeric medical grade silicone polymers and "soft" or elastomeric medical grade polyurethane polymers. The "soft" polymers may have a Shore A Hardness of between about 20 and about 60, more desirably between about 30 and about 50. The Shore Hardness testing of soft plastics is most commonly measured by the Shore (Durometer) test using either the Shore A or Shore D scale. The Shore A scale is used for "softer" rubbers while the Shore D scale is used for "harder" ones. The Shore A Hardness is the relative hardness of elastic materials such as rubber or soft plastics can be determined with an instrument called a Shore A Durometer. If the indenter completely penetrates the sample, a reading of 0 is obtained, and if no penetration occurs, a reading of 100 results. The reading is dimensionless.

The Shore hardness is measured with an apparatus known as a Durometer and is sometimes also referred to as Durometer Hardness. The hardness value is determined by the penetration of the Durometer indenter foot into the sample. Because of the resilience of rubbers and plastics, the hardness reading may change over time so the indentation time is sometimes reported along with the hardness number. The ASTM test number is ASTM D2240 while the analogous ISO test method is ISO 868.

The flexible sleeve may have a color or pigment integrated into the material forming the sleeve. Alternatively and/or additionally, the flexible sleeve may have a coating or layer of color on the exterior of the sleeve or on the interior of the sleeve. For example, the flexible sleeve may incorporate or be coated with a generally bright, fluorescent color that is readily visible and easy to identify. Examples of these colors include, but are not limited to, yellow, orange, blue, green, red, purple and various intensities and combinations thereof.

In an embodiment of the invention, the flexible sleeve may have a first color such as, for example, green, appearing at its second surface 70 and a second color such as, for example, red, appearing at its first surface 68. The housing 52 may be transparent such that when the flexible sleeve is at the second axial position "D", the flexible sleeve everts at the rolling annular fold 78 such that the color of the second surface 70 (e.g., green) is primarily visible and the color of the first surface 68 (e.g., red) is minimally visible or not visible. This movement of the flexible sleeve to the second axial position "D" where the color of the second surface 70 (e.g., green) is primarily visible and the color of the first surface 68 (e.g., red) is minimally visible or not visible provides a very simple and reliable indication to a user that the pressure of fluid in the balloon is different from (i.e., above) a predetermined level of pressure. Alternatively and/or additionally, the movement of the flexible sleeve to the second axial position "D" where the color of the second surface 70 (e.g., green) is primarily visible and the color of the first surface 68 (e.g., red) is minimally visible or not visible provides a very simple and reliable indication to a user that the volume of the balloon is at or greater than a predetermined fill volume.

In such an embodiment, the housing 52 may be transparent such that when the flexible sleeve is at the first axial position "P", the flexible sleeve everts at the rolling annular fold 78 such that the color of the second surface 70 (e.g., green) is minimally visible or not visible and the color of the first surface 68 (e.g., red) is primarily visible. This movement of the flexible sleeve to the first axial position "P" where the color of the second surface 70 (e.g., green) is minimally visible or not visible and the color of the first surface 68 (e.g., red) is primarily visible provides a very simple and reliable indication to a user that the pressure of fluid in the balloon is different from (i.e., below) a predetermined level of pressure. Alternatively and/or additionally, the movement of the flexible sleeve to the first axial position "P" where the color of the second surface 70 (e.g., green) is minimally visible or not visible and the color of the first surface 68 (e.g., red) is primarily visible provides a very simple and reliable indication to a user that the volume of the balloon is below or less than a predetermined fill volume.

According to an aspect of the invention, the flexible sleeve 66 and the other components of the pre-biased indicator 22 may be sized to appropriately fit with the head 36 of the enteral feeding assembly 20. For example, the flexible sleeve 66 may have a length from the first end 72 to the furthest outward extent of the rolling annular fold 78 towards the second end 60 of the housing 52 that may range from about 6 mm to about 12 mm. As another example, the indicator sleeve may have a length from the first end 72 to the furthest extent of the rolling annular fold 78 of from about 7 mm to about 11 mm. As yet another example, the indicator sleeve may have a length from the first end 72 to the furthest extent of the rolling annular fold 78 of from about 8 mm to about 10 mm.

The diameter of the flexible sleeve may be from about 2 mm to about 10 mm. For example, the diameter of the flexible sleeve may be from about 3 mm to about 9 mm. As another example, the diameter of the flexible sleeve may be from about 4 mm to about 6 mm. While the diameter implies a circular cross-section, other cross-sectional geometries are contemplated. For example, the flexible sleeve may have an elliptical cross-section, oval cross section or even a hexagonal cross-section, an octagonal cross-section or the like provided such cross-sectional geometries do not interfere with the movement of the rolling annular fold or rolling annular-like fold in the case of non-circular geometries. For purposes of the present invention, the term rolling annular fold encompasses rolling annular-like folds that are based on non-circular geometries to the extent that such geometries allow the rolling fold to evert the flexible sleeve and function as described above.

In an aspect of the invention, the diameter of the flexible sleeve need not be uniform. For example, the diameter of the flexible sleeve may be smaller at the first end 72 of the flexible sleeve and larger towards the second end 74 of the flexible sleeve closer to the rolling annular fold 78 provided such a change in diameter does not interfere with the function of the rolling annular fold. Other non-uniformities of the flexible sleeve are contemplated provided they do not interfere with the operation of the sleeve and the rolling annular fold.

The flexible sleeve may be configured to travel between about 3 to about 10 mm. That is, the displacement of the first end 72 of the flexible sleeve from its first axial position "P" to its second axial position "D" may range from about 3 to about 10 mm. The larger distance provides greater visibility of the flexible sleeve and a more noticeable signal. The smaller distance provides for an even more compact pre-biased indicator. For example, the displacement of the first end 72 of the flexible sleeve from its first axial position "P" to its second axial position "D" may range from about 4 to about 7 mm. As another example, the displacement of the first end 72 of the flexible sleeve from its first axial position "P" to its second axial position "D" may range from about 4 to about 5 mm.

The biasing element 82 is desirably a spring such as, for example, a coil compression spring. It is contemplated that other resilient constructions could be used as the biasing element. These include flexible, resilient foams, metal strips, volute or secateur springs, conical springs and the like. Descriptions of conical springs may be found at, for example, U.S. Pat. No. 4,111,407 for "Conical Compression Spring". Generally speaking, the biasing element 82 is desirably a coil compression spring that may be characterized as having linear movement and a spring rate designed such that the spring rapidly deforms over a very small range of pressure to provide a very discrete signal that the pressure of a fluid in the balloon is different from the predetermined pressure of the spring.

The biasing element may desirably be sized so that it approaches full compression or solid compression (including any allowance for coil clash or similar property for other resilient structures) at a point at or just beyond which the flexible sleeve reaches its second axial position "D". Desirably, the biasing element is sized so that it approaches solid compression or full compression at a point which allows the flexible sleeve to compress sufficiently so it reaches its second axial position "D" and become hidden from view in the second end 60 of the housing 52 while providing a column of support for the flexible sleeve 66 so that the travel of the flexible sleeve much beyond the second axial position "D" is limited. This characteristic serves to prevent the flexible sleeve from extending far enough to the second end 60 of the housing to totally evert or flip inside-out and eliminate the rolling annular fold 78. If the rolling annular fold is eliminated, the indicator may fail to function properly and may fail to allow travel of the flexible sleeve 66 back to its first axial position "P" in response to pressure of fluid in the balloon that is lower than the predetermined level of pressure of the biasing element because the inverted flexible sleeve may provide sufficient resistance to the biasing element to keep it from reforming or reconstituting the rolling annular fold. By providing sufficient structure to maintain the rolling annular fold 78, the biasing element allows ease of motion in both directions between the first axial position "P" and the second axial position "D" so the flexible sleeve can rapidly respond if the pressure of fluid in the balloon deviates from the predetermined level of pressure of the biasing element.

In an aspect of the invention, the biasing element is desirably configured so that the change in axial position of the flexible sleeve that generates the discrete visual signal occurs over a relatively small change in the pressure of the fluid in the balloon. For example, the change in pressure sufficient to effect the change in axial position of the flexible sleeve may be between about 0.25 pounds per square inch and about 0.75 pound per square inch. As another example, the change in pressure sufficient to effect the change in axial position of the flexible sleeve may be between about 0.4 pounds per square inch and about 0.6 pound per square inch. As yet another example, the change in pressure sufficient to effect the change in axial position of the flexible sleeve may be about 0.5 pounds per square inch (approximately 3.5 kilopascals). This change in pressure is a change in relative pressure and represents a change in pressure relative to the surrounding ambient or atmospheric pressure.

Desirably, the spring rate of the biasing element is a linear spring rate and is expressed in terms of pounds-force per linear inch (lbs-force/inch). That is, the spring rate is the load, expressed in pounds-force, required to deflect (i.e., compress or expand) the spring by a distance of one inch. For example, if the spring rate is forty (40) lbs-force/inch, it would take ten (10) lbs-force to deflect (i.e., compress or expand) the spring 0.25 inch and it would take eighty (80) lbs-force to deflect (i.e., compress or expand) the spring two (2) inches. One (1) lb-force/inch is about 1.8 newtons/cm.

According to the invention, the spring rate may range from about 0.1 lbs-force/inch to about 1.0 lbs-force/inch (about 0.4 newtons/inch to about 4.5 newtons/inch or about 0.1 newtons/cm to about 1.8 newtons/cm). Desirably, the spring rate may range from about 0.13 lbs-force/inch to about 0.60 lbs-force/inch. More desirably, the spring rate may range from about 0.2 lbs-force/inch to about 0.45 lbs-force/inch. Even more desirably, the spring rate may range from about 0.25 lbs-force/inch to about 0.35 lbs-force/inch. For example, the spring rate may be about 0.3 lbs-force/inch.

Generally speaking, the flexible sleeve 66 should have sufficient softness that it does not meaningfully interfere with the spring rate. For example, the flexible sleeve may have a flexible, generally annular portion in which the thickness of the walls in that portion range from about 5 to about 30 mils (i.e., about 5 to about 30 thousandths of an inch or about 127 micrometers to about 760 micrometers). As another example, the thickness of the walls may range from about 10 to about 20 mils (i.e., about 250 micrometers to about 510 micrometers). As yet another example, the thickness of the walls may range from about 15 to about 20 mils (i.e., about 380 micrometers to about 510 micrometers). This thickness may be determined by conventional techniques using a digital contact device such as, for example a Mitutoyo Litematic Digimatic Measuring Unit in accordance with the appropriate standardized tests. In an aspect of the invention, it is contemplated that the thickness of the flexible sleeve may be selected to meaningfully complement the resistance of the biasing element to deformation to provide a combined predetermined pressure of deformation for the combination of the two components.

An important feature of the present invention is that it provides a discrete visual signal that the pressure of a fluid in an inflatable balloon is different from a predetermined level of pressure. Generally speaking, this is accomplished by having the biasing element selected to provide sufficient movement (e.g., linearly along the axial dimension of the housing) and responsiveness to pressure (e.g., a low spring rate) such that the biasing element rapidly deforms over a very small range of pressure change to provide a discrete, distinct signal that the pressure of a fluid in the balloon is different from the predetermined pressure of the biasing element and/or that the volume of the balloon is different from the predetermined fill volume. Such a discrete visual signal may be characterized as a "binary" signal. That is, the pressure is either greater than (or equal to) the predetermined level of pressure which provides one output from the pre-biased indicator or the pressure is lower than the predetermined level of pressure which provides a different output from the pre-biased indicator. Alternatively and/or additionally, the volume of the balloon is either greater than or equal to the predetermined fill volume which provides one output from the pre-biased indicator or the volume of the balloon is lower than the predetermined fill volume which provides a different output from the pre-biased indicator. This response is much easier to interpret than the relative and continuous expansion of pilot balloons, bellows and/or other indicators that provide an uninterrupted reading or display of the different levels of pressure of a fluid in a balloon.

Such a simple and easy to interpret indicator is described as "pre-biased" because it is configured to change its indicator display or signal in response to fluid pressure crossing a predetermined threshold pressure. This configuration is enabled by the use of an inflatable balloon having a predetermined fill volume. Generally speaking, a predetermined fill volume is a volume in a range with a lower limit at the volume of the balloon at the transition from its non-distended state to its distended state where the fluid in the balloon is first under pressure and an upper limit no more than about 1.5 times (i.e., 50 percent greater than) the volume of the balloon at the transition from its non-distended state to its distended state.

These balloons are markedly different from conventional elastic balloons made of materials that stretch from a relaxed or un-stretched condition to continuously stretch or distend under increasingly higher pressures to ten times to even twenty times or more of their initial un-stretched dimensions to reach a design fill volume of three (3) to five (5) milliliters and a maximum fill volume that typically ranges between about eight (8) to about ten (10) milliliters. In many instances, such elastic balloons may be overfilled to reach much greater volumes without significant build up in pressure to provide resistance to overfilling because of the elastic stretching of the material of the balloon. While it is possible to make an elastic balloon that has a shape or volume even when it is not inflated, such an elastic balloon would have little or no practical use for most medical devices and especially as retainer balloons for enteral feeding catheters because the balloons present additional volume and difficulty to pass through an opening such as a stoma.

As noted previous, an exemplary relationship between pressure and volume during the inflation of an elastic retainer balloon made of conventional "soft" or elastomeric medical grade silicone is illustrated in FIG. 1C. As can be seen, an immediate pressure change from zero or negligible pressure to between about 4 to 7 pounds per square inch (28 to 48 kilopascals) is needed to continuously stretch such exemplary conventional retainer balloons to a volume of even 1 milliliter. A pressure between about 5 to 10 pounds per square inch (34 to 69 kilopascals) is needed to continuously stretch such conventional "soft" or elastomeric medical grade silicone balloons to a volume of about 3 milliliters. While it may be possible to make some alterations to the distension or stretch characteristics of such conventional elastic balloons by modifying properties of the elastomeric materials or the thicknesses of the balloon walls, the pressure and volume relationship illustrated by FIG. 1C is generally representative. It is notable that the pressure and volume relationship can be characterized as non-linear.

Another important characteristic of such conventional "soft" or elastomeric balloons is that energy used to stretch the material of the balloon ten times or even twenty times or more of its initial un-stretched dimensions is retained or stored by the stretched elastomeric material. That stretched material exerts a retraction or recovery force that seeks to take the dimensions of the balloon substantially or completely back to its original un-stretched dimensions. Accordingly, if there is a leak or breach in the balloon or in another part of the system allowing fluid to escape, the pressure against the fluid in the balloon generated by the material of the balloon as it retracts will tend to empty the balloon very quickly.

The present invention employs the use of an inflatable balloon having a "predetermined fill volume" as defined above. Such balloons are expandable from an initially collapsed or non-distended state to reach a predetermined volume without any meaningful stretching or distending of the materials that form the balloon unlike conventional elastic balloons that require continuously increasing pressure to stretch ten times to even twenty times or more of their initial un-stretched dimensions and then recover substantially or completely to their original un-stretched dimensions as that pressure is removed. The predetermined fill volume is the volume of the balloon in a range with a lower limit at the volume of the balloon at the transition from its non-distended state to its distended state where the fluid in the balloon is first under pressure and an upper limit no more than about 1.5 times (i.e., 50 percent greater than) the volume of the balloon at the transition from its non-distended state to its distended state. As can be seen in FIG. 1C, elastic balloons lack a transition from a non-distended state to a distended state. If such a transition did exist, it would occur only during the earliest introduction of pressure to initiate stretching or continuous distension of the material of the balloon and would be far below the final deployed volume of the balloon.

In other words, an inflatable balloon having a predetermined fill volume is essentially an impervious, flexible bag or container having a relatively fixed size (i.e., fixed volume). When the balloon (i.e., bag) is empty, it is essentially in a collapsed state and has the potential to be filled with a fluid up to its fixed size. Filling is accomplished by introducing fluid into the balloon through the inflation valve of the enteral feeding assembly. As the balloon receives increasing volumes of fluid, the balloon transforms from a collapsed state to a distended state that generally corresponds to the particular distended profile of a balloon typically generated during the manufacture of the balloon in a molding, blowing, casting or similar process. Essentially no pressure is required to fill the balloon other than to drive the liquid through the inflation lumen and unfold the balloon because the material forming the balloon is not stretched or distended to reach its fixed or predetermined size. The "reserve volume" of the balloon is found at the transition between the balloon's non-distended state and distended state before the fluid in the balloon is under pressure. The pressure of fluid in the balloon increases when the balloon is filled past the reserve volume. The pressure of fluid in the balloon increases in a substantially linear relationship with additional increases in the volume of the balloon.

Various materials may used to form the inflatable balloon having a predetermined fill volume. These materials include, but are not limited to, polyurethane (PU), low-density polyethylene (LDPE), polyvinyl chloride (PVC), polyamide (PA), or polyethylene teraphthalate (PETP). Additionally, copolymer admixtures for modifying the characteristics of the material may be used, for example a low density polyethylene and ethylene-vinylacetate copolymer (LDPE-EVA), or blends of the above mentioned materials (e.g. PU with PVC or PU with PA) would be considered suitable for forming the inflatable balloon having a predetermined fill volume. Other materials would also be suitable so long as they exhibit properties enabling them to be processed into an inflatable retention balloon having thin walls on the order of about 5 to about 100 micrometers as measured in the central region of the balloon. This thickness may be determined by conventional techniques utilizing a digital contact device such as, for example a Mitutoyo Litematic Digimatic Measuring Unit in accordance with the appropriate standardized tests. Desirably, the balloons may have thin walls desirably in a range of between about 5 to about 50 micrometers, even more desirably, between about 5 to about 25 micrometers. Suitable materials should possess properties enabling them to be processed into an inflatable retention balloon having micro thin walls which do not deform elastically to such a degree that they are enabled to slip through the an opening. In contrast, conventional silicone balloons have wall thicknesses of about 250 micrometers or even greater.

Figure 7A:
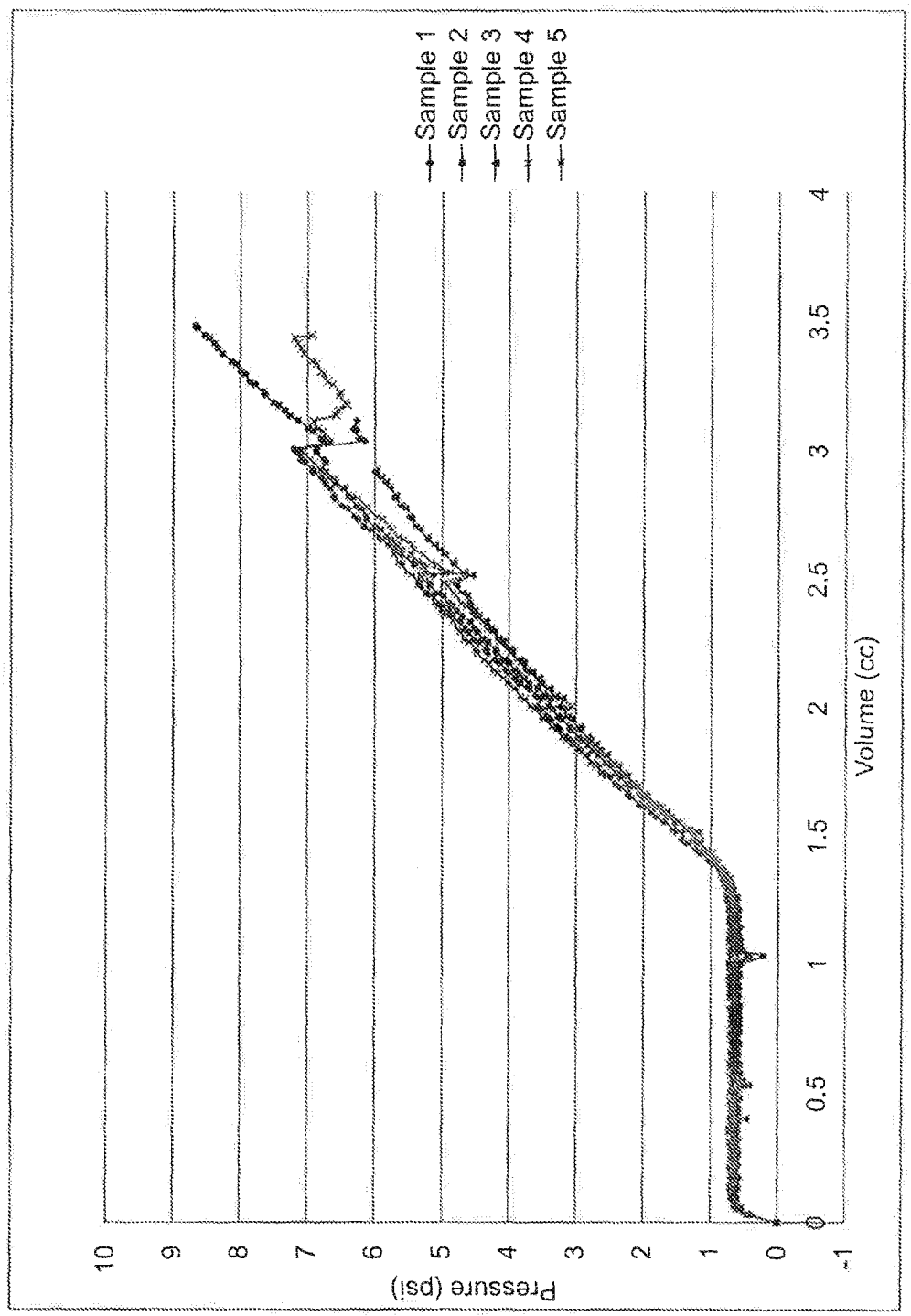
FIGS. 7A and 7B are illustrations of a feature of an exemplary enteral feeding catheter assembly incorporating an indicator.
Figure 7B:
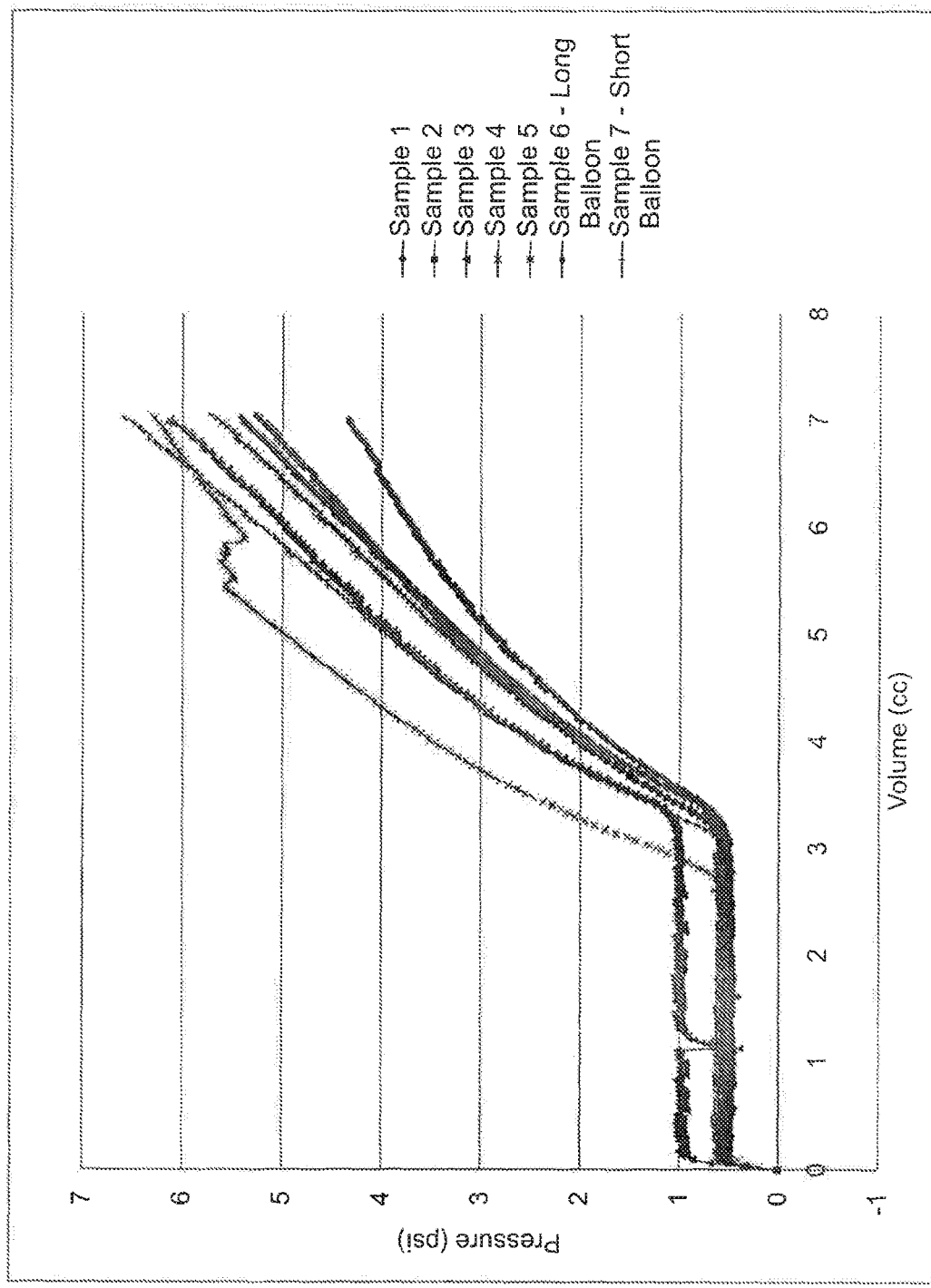

FIGS. 7A and 7B are illustrations showing exemplary relationships between the balloon volume and the pressure of a fluid inside a balloon having a predetermined fill volume. These illustrations show the transition between the non-distended state and distended state of such as balloon.

FIG. 7A illustrates the relationship between pressure and volume for five samples of balloons having a predetermined fill volume of approximately two (2) milliliters. As can be seen in FIG. 7A, the pressure profiles are essentially negligible during filling of the balloons to their predetermined fill volumes. The slight pressure that is encountered is due to the driving force needed to get the fluid through the inflation lumen and to unfold the collapsed balloon. At the transition from the non-distended state to the distended state which occurs at a volume just above about 1.5 milliliters (i.e., about 1.6 to about 1.7 milliliters), the pressures begins to increase linearly.

FIG. 7B illustrates the relationship between pressure and volume for seven samples of balloons having a predetermined fill volume of approximately 5 milliliters. As can be seen in FIG. 7B, the pressure profiles are essentially negligible during filling of the balloons to their predetermined fill volumes. The slight pressure that is encountered is due to the driving force needed to get the fluid through the inflation lumen and to unfold the collapsed balloon. At the transition from the non-distended state to the distended state which occurs at a volume just above about 3.5 milliliters (i.e., about 3.6 to about 3.7 milliliters), the pressures begins in to increase linearly.

Because of the relationship between pressure and volume that exists for balloons having predetermined fill volumes as generally represented in FIGS. 7A and 7B, the deformation pressure of the pre-biased indicator may be set much lower than would be possible for conventional elastic balloons which must continually distend under increasing pressure. The pre-biased indicator responds to the change in pressure that begins at the transition from the non-distended state to the distended state. The predetermined level of pressure which corresponds to the predetermined fill volume of the balloon may be set at the transition from the non-distended state to the distended state or it may be set to a pressure that corresponds to a volume not more than about fifty percent (50%) greater. During filling of the balloon, the pre-biased indicator provides a discrete visual signal that the predetermined fill volume has been reached. After the balloon is filled, the pre-biased indicator provides a discrete visual signal that the balloon has lost pressure or volume and may be leaking. An advantage of utilizing such balloons having a predetermined fill volume as described above is that if there is a leak or breach in the balloon or in another part of the system allowing fluid to escape, the fact that the balloon is un-stretched or un-distended at its predetermined fill volume means there should be very little or no pressure or driving force from the balloon causing additional fluid to leak out—unlike conventional elastic balloons that store the energy of their stretched condition to retract back to their initial un-stretched condition.

An aspect of the present invention encompasses an indicator assembly for use in medical products, especially medical products having a head located outside the human body and an inflatable retainer balloon for deployment within a lumen of a human body. The indicator assembly includes an inflatable thin-walled balloon having a predetermined fill volume. In an aspect of the invention, a thin-wall balloon formed of a material such as, for example, polyurethane lacks rigidity sufficient for the balloon to serve as an anchor when it does not contain fluid such as a liquid or, in some situations, a gas. Generally speaking, this can correspond to balloons having thin walls with a thickness of about 100 micrometers or less. Desirably, the balloons have a wall thickness of about 50 micrometers or less. More desirably, the balloons have a wall thickness between about 5 to about 50 micrometers, more desirably between about 5 to about 25 micrometers, even more desirably, between about 5 to about 15 micrometers.

The balloon is configured to contain a fluid under pressure upon inflation to its predetermined fill volume and after inflation further configured to contain a reserve volume of fluid when the fluid is no longer under pressure. The reserve volume is less than the predetermined fill volume and reflects a volume of liquid that is retained in the balloon at about the transition from its non-distended state to its distended state. This relationship or characteristic is illustrated by FIGS. 7A and 7B as discussed above. Desirably, the pressure of the fluid upon inflation to the predetermined fill volume is at relatively low pressures such as, for example, 4 pounds per square inch (28 kilopascals) or less. For example, the pressure of the fluid upon inflation to the predetermined fill volume may be between about 1 to about 3.5 pounds per square inch (psi) (approximately 7 to about 25 kilopascals). As another example, the pressure of the fluid upon inflation to the predetermined fill volume may be between about 2 to about 3 pounds per square inch (psi) (approximately 14 to about 21 kilopascals).

The indicator assembly also includes an indicator that provides only a first discrete visual signal when the balloon is inflated to its predetermined fill volume and a second discrete visual signal when the fluid in the balloon is no longer under pressure, with no signal of other inflation states therebetween. That is, the indicator provides a signal of only two states of the balloon—that it is at its predetermined fill volume and that the fluid in the balloon is no longer under pressure. The general structure of an exemplary indicator is described above and is illustrated at, for example, in FIGS. 2-4, 5A, 5B, 6A and 6B.

According to the invention, the second discrete visual signal provides warning that the balloon volume has reached the reserve volume. Because the balloon is configured to hold a volume of fluid even when the balloon is not under pressure (unless there is a catastrophic failure of the wall of the balloon or connection between the balloon and the device), a user will have a period of time to re-inflate the balloon or replace the device without having to worry about the balloon immediately failing to anchor the device.

Generally speaking, the predetermined fill volume is desirably from about 1.01 to about 1.5 times greater than the reserve volume (i.e., about 1 percent to about 50 percent greater than the volume of the balloon at the transition from its non-distended state to its distended state). For example, the predetermined fill volume may be from about 1.05 to about 1.4 times greater than the reserve volume (i.e., about 5 percent to about 40 percent greater than the volume of the balloon at the transition from its non-distended state to its distended state). As another example, the predetermined fill volume may be from about 1.1 to about 1.3 times greater than the reserve volume (i.e., about 10 percent to about 30 percent greater than the volume of the balloon at the transition from its non-distended state to its distended state).

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. An enteral feeding catheter assembly comprising:
   a catheter having a proximal end, a distal end, and catheter walls defining a catheter lumen;
   a base located at the proximal end of the catheter, the base defining an opening to the catheter lumen, the base having a first end and a second end;
   an inflatable balloon having a predetermined fill volume, the balloon located at a distal end of the catheter;
   an inflation valve located on the base, the inflation valve in fluid communication with the balloon through an inflation lumen defined by the catheter walls;
   a pre-biased indicator located on the base in fluid communication with the balloon, the pre-biased indicator configured to provide a discrete visual signal that the pressure of a fluid in the balloon is different from a predetermined level of pressure or the volume of the balloon is different from the predetermined fill volume; and
   the indicator in direct fluid communication with the retainer balloon by way of an indicator lumen that extends between the retention balloon and the indicator such that the retention balloon is supplied with the fluid under pressure prior to the indicator.

2. The enteral feeding catheter assembly of claim 1, wherein the pre-biased indicator comprises:
   a housing having a first end, a second end, one or more walls defining an interior channel, and an axial dimension, the first end of the housing being in fluid communication with the inflatable balloon via the indicator lumen that extends between the retention balloon and the indicator, and at least a portion of the housing being transparent or translucent;
   a flexible sleeve positioned within the interior channel of the housing, the flexible sleeve comprising: a first surface, an opposed second surface, a first end located within the interior channel of the housing near the first end of the housing and in fluid communication with the inflatable balloon, a second end sealingly engaged with the housing, and a flexible, generally annular portion joining the first end and second end of the sleeve, the annular portion defining a rolling annular fold intermediate the first end and the second end such that at least a portion of the first surface of the flexible sleeve is generally adjacent the one or more housing walls and at least a portion of the second surface of the flexible sleeve defines a sleeve cavity; and
   a biasing element located at least partially within the sleeve cavity and between the first end of the housing and the second end of the housing, the biasing element being configured to deform at a predetermined pressure so the first end of the flexible sleeve moves from a first axial position to at least a second axial position to provide a discrete visual signal that the pressure of a fluid in the balloon is different from the predetermined level of pressure or the volume of the balloon is different from the predetermined fill volume; and
   wherein the movement of the flexible sleeve in an axial direction causes a portion of the second surface of the flexible sleeve to evert at the rolling annular fold so that it becomes directly adjacent the one or more housing walls.

3. The enteral feeding catheter assembly of claim 1, where in the inflation valve is located on the first end of the base and the indicator is located on the second end of the base.

4. The enteral feeding catheter assembly of claim 1, wherein the pre-biased indicator is configured to provide a discrete visual signal that the pressure of the fluid in the balloon is less than a predetermined level of pressure or the volume of the balloon is less than the predetermined fill volume.

5. The enteral feeding catheter assembly of claim 1, wherein the pre-biased indicator is configured to provide a discrete visual signal that the pressure of the fluid in the balloon is greater than a predetermined level of pressure or the volume of the balloon is greater than the predetermined fill volume.

6. A balloon catheter device, the balloon catheter comprising:

a catheter having a proximal end, a distal end, and catheter walls defining a catheter lumen;

a base located at the proximal end of the catheter defining an opening to the catheter lumen;

an inflatable balloon having a predetermined fill volume, the balloon located at a distal end of the catheter and configured to contain a fluid under pressure;

an inflation valve located on the base, the inflation valve in fluid communication with the balloon;

a pre-biased pressure indicator in fluid communication with the balloon, the pre-biased pressure indicator configured to provide a discrete visual signal that the pressure of the fluid in the balloon is different from a predetermined level of pressure or the volume of the balloon is different from the predetermined fill volume; and the indicator in direct fluid communication with the retainer balloon by way of an indicator lumen that extends between the retention balloon and the indicator such that the retention balloon is supplied with the fluid under pressure prior to the indicator.

7. The device of claim 6, wherein the pre-biased indicator comprises a housing having an axial dimension, a flexible sleeve fitted within the housing, and a biasing element in communication with the flexible sleeve, the biasing element being configured to deform at a predetermined pressure so the flexible sleeve travels along the axis of the housing from a first axial position to a second axial position.

8. The device of claim 6, where in the pre-biased indicator is located on the base at the proximal end of the catheter.

9. The device of claim 7, wherein the first position of the flexible sleeve provides a discrete visual signal that the pressure of the fluid in the balloon is less than the predetermined level of pressure or the volume of the balloon is less than the predetermined fill volume.

10. The device of claim 7, wherein the second position of the flexible sleeve provides a discrete visual signal that the pressure of the fluid in the balloon is greater than the predetermined level of pressure or the volume of the balloon is greater than the predetermined fill volume.

11. The device of claim 7, wherein the flexible sleeve is visible through at least a portion of the housing while the flexible sleeve is in its first position.

12. The device of claim 6, wherein the catheter defines an inflation lumen and the balloon is in fluid communication with the inflation valve through the inflation lumen.

* * * * *